United States Patent [19]

Bickford

[11] 4,353,366

[45] Oct. 12, 1982

[54] CARBON DIOXIDE ABSORBER

[76] Inventor: Allan M. Bickford, 1581 Hubbard Rd., East Aurora, N.Y. 14052

[21] Appl. No.: 171,330

[22] Filed: Jul. 23, 1980

[51] Int. Cl.³ .............................................. A61M 16/00
[52] U.S. Cl. ............................ 128/205.12; 128/205.17; 55/DIG. 33; 210/443
[58] Field of Search ..................... 128/205.12, 202.26, 128/205.27, 205.28, 205.17; 55/502, 494, DIG. 33, DIG. 35; 210/443

[56] References Cited

U.S. PATENT DOCUMENTS

| | | | |
|---|---|---|---|
| 2,041,406 | 5/1936 | Foregger | 128/205.12 |
| 2,388,533 | 11/1945 | Edmondson et al. | 128/203.28 |
| 2,837,413 | 6/1958 | Hay | 128/205.28 |
| 3,088,810 | 12/1958 | Hay | 23/252 |
| 4,108,775 | 8/1978 | Wilkes et al. | 210/440 |
| 4,120,794 | 10/1978 | Taylor | 210/440 |
| 4,232,667 | 11/1980 | Chalon et al. | 128/203.26 |

FOREIGN PATENT DOCUMENTS 630481 10/1949 United Kingdom ........... 128/205.12

OTHER PUBLICATIONS

Dupaco, Twin Canister Circle Absorber, Brochure 705.

*Primary Examiner*—Henry J. Recla
*Attorney, Agent, or Firm*—Bean, Kauffman & Bean

[57] ABSTRACT

A carbon dioxide absorbing apparatus having a base containing adjacent inhalation and exhalation passages, a through opening or passage centrally located on the base and in communication with the inhalation passage, a gasket located on the base having a raised lip annular opening coaxial with the through opening, a cannister of carbon dioxide absorbing material resting on the raised lip of the gasket and a cover surrounding the cannister defining an annular passage therebetween which is in communication with the exhalation passage. Pins are removably provided along one or more circles of varying diameters on the base to orient the cannister in proper operative position.

14 Claims, 4 Drawing Figures

CARBON DIOXIDE ABSORBER

BACKGROUND OF THE INVENTION

The present invention relates to carbon dioxide absorbers and, more particularly, to an absorber for removing carbon dioxide from respiratory gases to patients undergoing anesthesia.

Presently known carbon dioxide absorbers are typified by that disclosed in U.S. Pat. No. 3,088,810, which generally comprise upper and lower functional assemblies with one or more cannisters of a carbon dioxide absorbent material sandwiched therebetween. The exhaled respiratory gases from the patient flow from the upper assembly through the cannister or cannisters for removal of carbon dioxide therefrom and thence from the lower assembly through external connectors and an external conduit or pipe back to or through the upper assembly to a point adjacent to that from which the exhaled gases entered the upper assembly. Patient breathing tubes emanating from a face mask or the like are connected to the upper assembly at the adjacent locations where the exhaled gases entered, and the inhaled gases exited from, the upper assembly.

This type of absorber is costly and complex, requiring an inordinately large number of parts considering the relatively simple functions to be performed. For example, in addition to the external conduit between the upper and lower assemblies, an elaborate clamping arrangement is required to secure and retain the cannister or cannisters in their operative positions. The clamping structure must also be adjustable to accommodate one or two cannisters of varying sizes. The external conduit or pipe must be similarly adjustable in length, usually by means of flexible conduits or telescoping sections. Numerous machined, polished and chrome-plated connectors and fittings are also required, further adding to the cost and complexity of presently known absorbers.

Additionally, the upper and lower assemblies are usually fabricated of brass to which the fittings and connectors are generally soldered. This type of arrangement renders currently known absorbers and the parts thereof difficult to disassemble for routine cleaning, maintenance and/or repair.

SUMMARY OF THE INVENTION

The foregoing problems and disadvantages, as well as others, of prior carbon dioxide absorbers are overcome according to the teachings of the present invention, which provides a carbon dioxide absorbing unit that is simply constructed, efficient, easy to clean and incorporates a minimum number of structural components while, at the same time, remaining extremely versatile and adaptable to one or more cannisters of standard as well as non-standard sizes.

Basically, the carbon dioxide absorber according to the present invention incorporates a unitary base which serves not only as the mount for all other components of the apparatus, but also serves as the only component to which all the external flow connectors are affixed. This greatly reduces the bulk, complexity and cost of the absorber while, at the same time, provides for a lightweight and compact arrangement.

According to the invention the base is provided with means for permitting one or more cannisters of standard or non-standard size to be supported thereby in the proper functional position without the necessity of any clamping structure, whereby the cannister or cannisters can be quickly attached or removed and replaced.

In essence, the present invention provides a carbon dioxide absorber having a base, a cover removably attached to the base in surrounding relation to at least one carbon dioxide absorbing cannister that is supported upon the base defining an annular passage between the cover and the cannister, an exhalation or inlet passage in the base communicating with the annular passage for supplying exhaled respiratory gases to the cannister, an opening in the base adjacent the cannister for receiving the gases passing therethrough and an inhalation or outlet passage in the base in close proximity to the exhalation passage, the inhalation passage being in fluid communication with the opening adjacent the cannister.

BRIEF DESCRIPTION OF THE DRAWINGS

For a fuller understanding of the present invention reference should be made to the following detailed description thereof when taken in conjunction with the accompanying drawings, wherein.

DESCRIPTION OF THE PREFERRED EMBODIMENT

Figure 1:
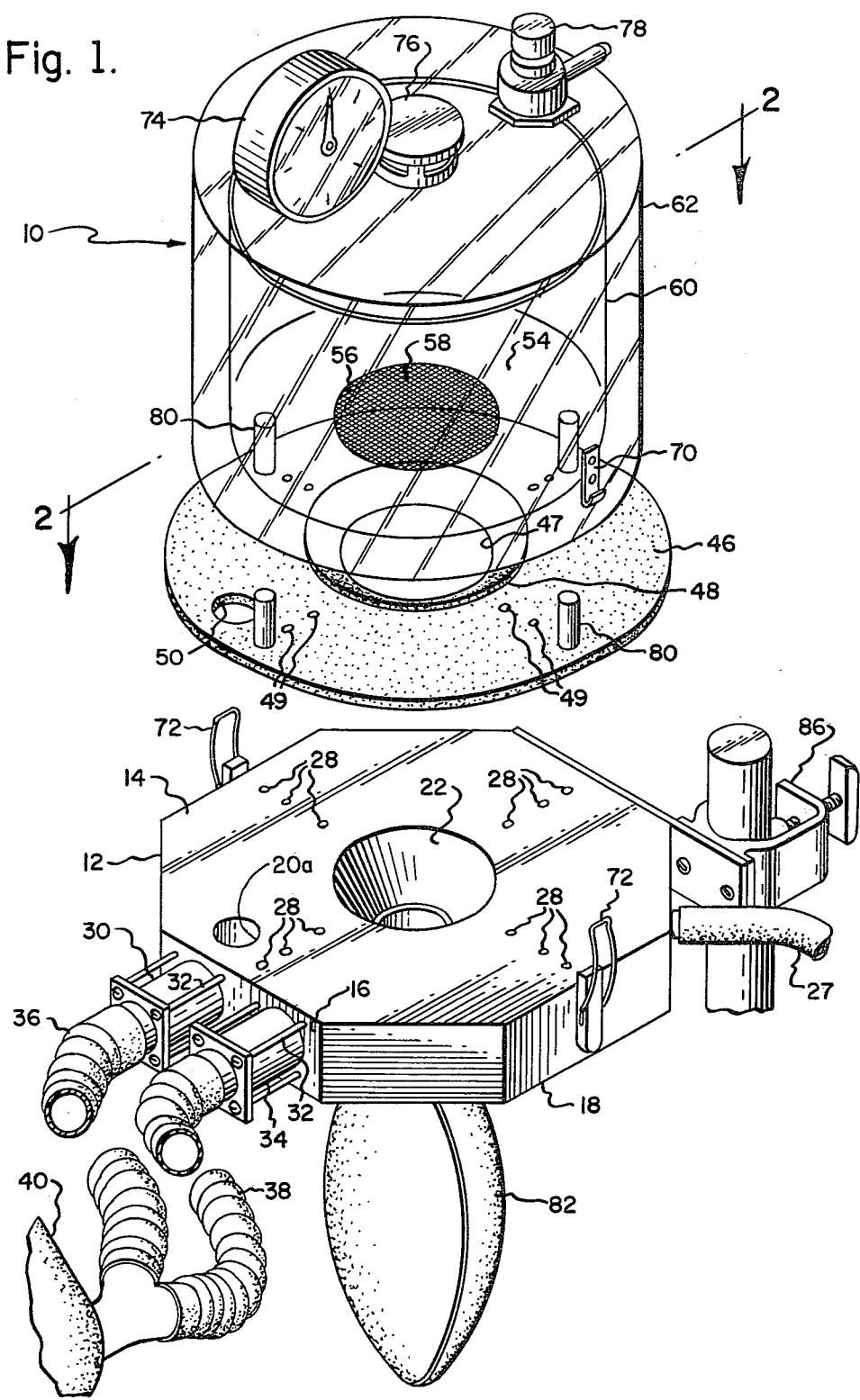
FIG. 1 is a pictorial exploded view depicting the various components of the carbon dioxide absorbing apparatus of the present invention.
Figure 3:
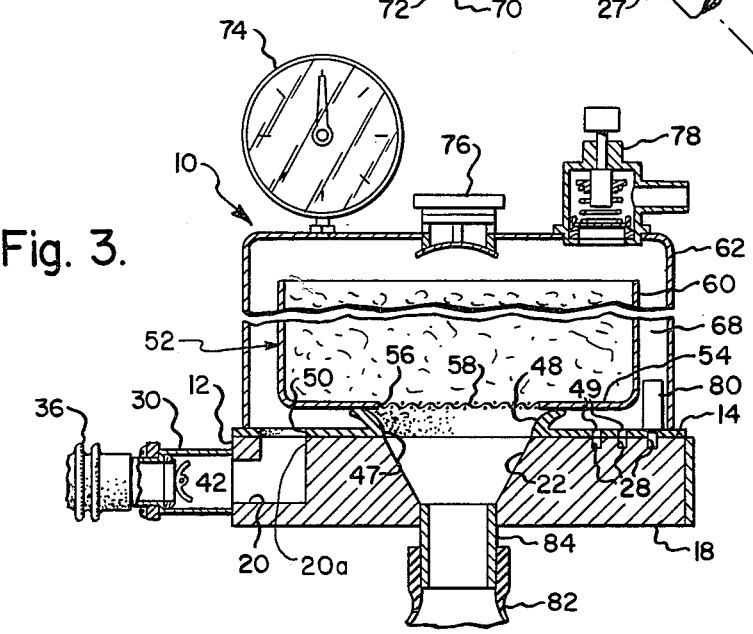
FIG. 3 is a partial fragmentary sectional view taken along line 3—3 of FIG. 2.

Referring now to the drawings, the carbon dioxide absorbing apparatus according to the invention is generally depicted at 10 and is shown as comprising a unitary base 12 having a substantially planar upper surface 14 and a depending cylindrical side wall 16 terminating in a bottom planar surface 18. Base 12 may be fabricated from any suitable material such as metal or plastic and, as illustrated in FIG. 3, has a right-angled inlet or exhalation passage 20 extending from side wall 16 to the upper surface 14, wherein the upper end 20a of passage 20 is offset relative to the center of the upper surface. Opening means are centrally provided on the base in the form of a substantially conical or funnel-shaped passage 22 extending from the upper surface 14 thereof to bottom surface 18. An outlet or inhalation passage 24 communicates with passage 22, extending therefrom to side wall 16 adjacent to and in close proximity with inlet passage 20. Also in communication with passage 22, intermediate the ends thereof, is an auxiliary gas supply passage 26 entering through a side wall of the base and to which an external conduit or tube 27 may be removably secured. As best seen in FIG. 1, base 12 is provided in the upper surface thereof with a plurality of additional openings 28 arranged along circles of varying diameters and radially spaced from passage 22. The purpose of these openings will become apparent hereinbelow.

An inlet check valve housing 30 is removably secured to the base in abutting relation to passage 20 by any suitable means such as bolts 32. Similarly, an outlet check valve housing 34 is removably secured to the base in abutting relation to outlet passage 24. Conventional breathing tubes 36 and 38 have first ends connected to check valve housings 30 and 34, respectively, and second ends joined in a "Y" fitting of a conventional patient face mask 40 or the like. Any suitable type of check valve means 42 may be located within housing 30 to permit only one-way flow of exhaled gases from breathing tube 36 to inlet passage 20. Similarly, check valve means 44 is provided in housing 34 to permit only one-way flow of inhalation gases from outlet passage 24 to breathing tube 38 for inhalation by a patient. Thus, passage 20 and passage 24 with its associated passage 22 may be considered as providing a pair of passage means having first ends arranged to open through side wall 16 for flow communication with breathing tubes 36 and 38 via check valves 42 and 44 and second ends arranged to open through upper surface 14.

Support means, which is preferably in the form of a gasket 46 fabricated of a suitable resiliently deformable material, such as rubber, is mounted on the upper surface of base 12. Gasket 46 is formed with a central opening 47, which is disposed for alignment with the upper end of passage 22 and bounded by a raised, resiliently deformable annular lip 48; a plurality of openings 49, which are disposed for alignment one with each of openings 28; and an offset opening 50, which is disposed for alignment with the upper end 20a of inlet passage 20.

A substantially cup-shaped cannister 52 is best shown in FIG. 3 as being filled with a charge of a suitable carbon dioxide absorbing material, such as soda lime or other metallic hydroxide in particulate form. Cannister 52 includes a bottom wall 54 having a centrally located outlet opening 56 fitted with a screen 58 of suitable mesh size to prevent the flow of carbon dioxide absorbing material downwardly therethrough; and a cylindrical side wall 60, which serves to define an open upper end or inlet opening permitting the filling of the cannister with a charge of material and the introduction of gases from which carbon dioxide is to be removed. As will be apparent from viewing FIG. 3, outlet opening 56 is sized to permit placement thereof within the confines of annular lip 48 to provide for flow communication between the interior of cannister 52 and the upper end of passageway 22; the weight of the cannister and/or its contents being sufficient to resiliently deform the annular lip such that it provides a fluid seal between base 12 and cannister bottom wall 54 in order to prevent admission of non-treated gases into passage 22.

Although a single cannister is illustrated, it is apparent that stacked cannisters could be utilized as is well known in this art. Moreover, as will become apparent hereinbelow, commercially available, pre-charged cannisters of varying sizes can be also employed. In any event, the cannister is preferably fabricated at least in part of a transparent material, such as glass or plastic, to permit visual inspection of the absorbing material contained within, since standard commercially available carbon dioxide absorbers contain an indicator which changes color upon exhaustion of the active absorbing ingredients.

Figure 2:
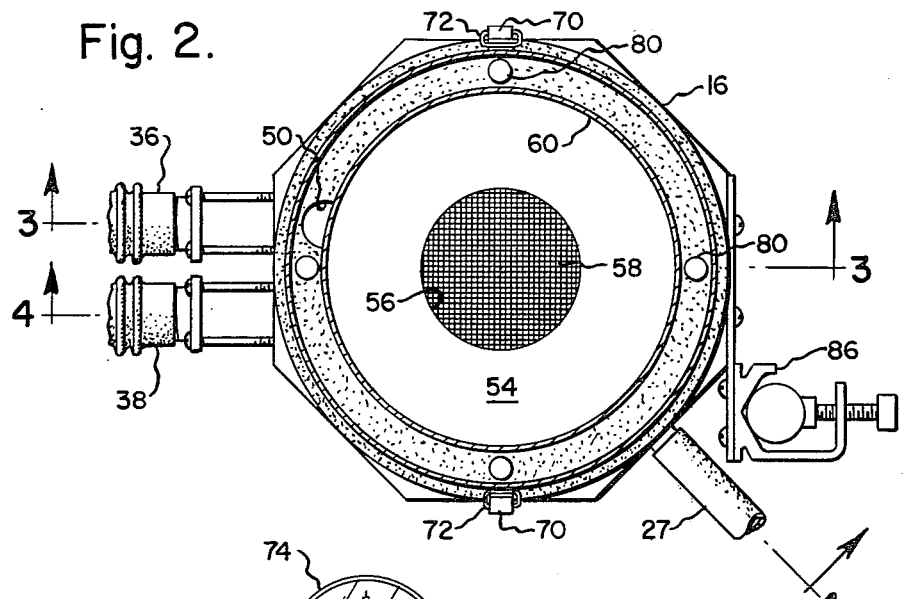
FIG. 2 is a sectional view of the assembled apparatus of FIG. 1 taken along line 2—2 thereof.

A generally cylindrical cover 62 having a closed upper wall 64 and a depending side wall 66 defining an open bottom end in contact with gasket 46 is located in spaced, surrounding relation to cannister 52 to thereby define an annular passage 68 therebetween. Upper wall 64 is sufficiently spaced from cannister 52 to permit free flow of exhaled gases between annular passage 68 and the interior of the cannister. Latch means are provided on the cover 62 and the base 12 to secure the cover in its operative position and to force the same into intimate compressing contact with the gasket 46 for sealing purposes. As illustrated in FIGS. 1 and 2, such latch means may conveniently take the form of a toggle latch assembly having the hooks thereof affixed to the cover at diametrically opposed points thereon, with the cooperating eyes 72 thereof being located at corresponding points on the base. Of course, any other type of known means can be provided to permit quick and secure attachment of the cover to the base. The cover is preferably fabricated of a transparent material such as glass or plastic to permit visual inspection of the cannister and the carbon dioxide absorbing material.

Suitably mounted on the top wall 64 of the cover is a gage 74, a vacuum relief valve 76 and a pressure relief valve 78, all of conventional construction. Gage 74 functions to indicate not only positive pressures within the cover but negative pressures as well, whereas vacuum relief valve 76 functions to permit air at atmospheric pressure to break any vacuum that may exist to thereby prevent patient suffocation, and relief valve 78 functions to vent to atmosphere any abnormally high pressures that may develop within the cover, such as those intermittent over-pressures that may be caused by patient exhalation at the same time as auxiliary gases are supplied via conduit 27.

Figure 4:
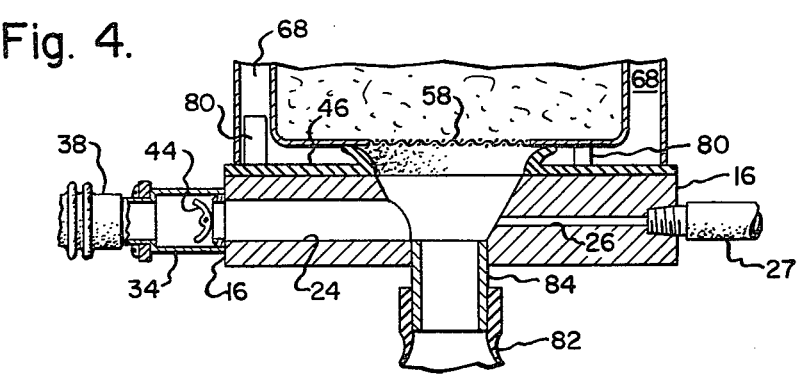
FIG. 4 is a fragmentary sectional view taken along line 4—4 of FIG. 2.

To properly orient the cover and the cannister in their operative locations on the base, positioning means are provided in the form of a plurality of pins 80 that may be removably fitted into base openings 28, referred to previously. As best seen in FIGS. 3 and 4, these pins are located in the annular passage 68 between the cover and the cannister and project upwardly from the base 12. In the position shown, the pins 80 serve to guide the cannister into proper position on the raised annular lip 48 to thereafter prevent undesired lateral displacements thereof. In this position the pins 80 also serve to permit the cover to be easily oriented into its proper central position on the base. In as much as the pins 80 are removable and the openings 28 in the base are arranged along circles of varying diameters, different sized cannisters can be easily accommodated by simply changing the location of the pins. This feature enables the structure of the present invention to be adaptable to standard as well as non-standard sized cannisters. The pins 80 may also function to secure the gasket 46 to the base.

A conventional, flexible or resilient material reservoir or "breathing bag" 82 is removably secured to the bottom end of funnel-shaped passage 22 by means of a coupling sleeve 84 or the like.

The whole assembly may be mounted on an anesthesia machine (not illustrated) or on an adjacent stand by means of an adjustable bracket 86 or the like secured to the base.

In the operation of the carbon dioxide absorbing apparatus of the present invention, exhaled gases from a patient flow from breathing tube 36, through check valve 42, through passage 20 and annular passage 68 to the top of cannister 52 and thence downwardly through the carbon dioxide absorbing material, where the carbon dioxide is removed. The gases, substantially free of carbon dioxide, then flow through meshed screen 58 downwardly through passage 22 and into reservoir or accumulator 82. Upon inhalation by the patient, gas flows from the reservoir through outlet passage 24, through check valve 44 and breathing tube 38 to the patient. Auxiliary or supplemental make-up gases such as oxygen or anesthesia may be simultaneously supplied to the patient through auxiliary supply passage 26. Since these gases may be supplied during exhalation, as well as during inhalation, temporary overpressures may develop which will cause the relief valve 78 to frequently open for the venting thereof to atmosphere.

Although a preferred embodiment of the present invention has been disclosed and described, changes will obviously occur to those skilled in the art. It is therefore intended that this invention is to be limited only by the scope of the appended claims.

What is claimed is:

1. Apparatus for removing carbon dioxide from respiratory gases, comprising:
   a base;
   a cannister for containing a charge of carbon dioxide absorbing material and having upper inlet and lower outlet openings for permitting flow of gases therethrough in contact with said absorbing material;
   a gasket formed of resiliently deformable material and positioned on said base for supporting said cannister, said gasket having an opening bounded by a raised annular lip for providing a fluid seal with said cannister outwardly of said outlet opening;
   a cover removably attached in fluid sealed relationship to said base in a spaced surrounding relationship to said cannister thereby enclosing said cannister, said cover and said cannister cooperating to provide a fluid flow passage therebetween with said fluid flow passage being arranged for flow communication with said inlet opening;
   inlet passage means in said base in flow communication with said fluid flow passage for supplying the same with gases from which carbon dioxide is to be removed;
   opening means in said base and arranged for flow communication with said outlet opening through said opening of said gasket; and
   outlet passage means in said base arranged in fluid communication with said opening means for withdrawing gases from which carbon dioxide has been removed.

2. The apparatus according to claim 1, wherein said base has upper and bottom surfaces and a side wall extending therebetween, said opening means comprises a passage extending vertically through said base between said upper and bottom surfaces and there is further provided, a flexible gas reservoir attached to said base to depend below said bottom surface and for flow communication with said last mentioned passage.

3. The apparatus according to claim 2, wherein said inlet passage means has opposite ends thereof arranged to open through said side wall and said upper surface, said outlet passage means has opposite ends thereof arranged to open through said side wall and said last mentioned passage, check valve means are fixed to said side wall exteriorly of said base for communicating with said inlet passage means for permitting only one-way flow to said annular passage; and
   check valve means are fixed to said side wall exteriorly of said base for communicating with said outlet passage means for permitting only one-flow from said opening means through said outlet passage means, and the first and second said check valve means are disposed in a side by side relationship.

4. The apparatus according to claim 1, wherein there is further provided, latch means on said cover and said base for securing said cover to said base and for compressing said gasket.

5. Apparatus for removing carbon dioxide from respiratory gases, comprising:
   a base;
   a cannister for containing a charge of carbon dioxide absorbing material and having upper inlet and lower outlet openings for permitting flow of gases therethrough in contact with said absorbing material;
   support means on said base for supporting said cannister and for providing a fluid seal with said cannister outwardly of said outlet opening;
   a cover removably attached in fluid sealed relationship to said base in a spaced surrounding relationship to said cannister thereby enclosing said cannister, said cover and said cannister cooperating to provide a fluid flow passage therebetween with said fluid flow passage being arranged for flow communication with said inlet opening;
   inlet passage means in said base in flow communication with said fluid flow passage for supplying the same with gases from which carbon dioxide is to be removed;
   opening means in said base adjacent said support means and arranged for flow communication with said outlet opening;
   outlet passage means in said base in flow communication with said opening means for withdrawing gases from which carbon dioxide has been removed; and
   positioning means removably affixed to said base and arranged in said fluid flow passage for positioning said outlet opening in alignment with said opening means, said base is provided with additional openings disposed outwardly of said opening means, and said positioning means comprises a plurality of pins fitted within said additional openings.

6. The apparatus according to claim 5, wherein said additional openings on said base are arranged along a plurality of circles of varying diameters and radially spaced from said opening means.

7. Apparatus for removing carbon dioxide from respiratory gases, comprising:
   a base;
   a cannister for containing a charge of carbon dioxide absorbing material and having upper inlet and lower outlet openings for permitting flow of gases therebetween in contact with said absorbing material;
   a gasket formed of resiliently deformable material and positioned on said base for supporting said cannister, said gasket having an opening bounded by a raised annular lip for providing a fluid seal with said cannister outwardly of said outlet opening;
   a cover removably attached in fluid sealed relationship to said base in a spaced surrounding relationship to said cannister thereby enclosing said cannister, said cover and said cannister cooperating to provide a fluid flow passage therebetween with said fluid flow passage being arranged for flow communication with said inlet opening;
   inlet passage means in said base in flow communication with said fluid flow passage for supplying the same with gases from which carbon dioxide is to be removed;
   opening means in said base arranged for flow communication with said outlet opening through said opening of said gasket;

outlet passage means in said base in flow communication with said opening means for withdrawing gases from which carbon dioxide has been removed; and positioning means are removably fixed to said base and located within said fluid flow passage for positioning said cannister for engagement with said annular lip outwardly of said outlet opening and for securing said gasket to said base.

8. Apparatus for removing carbon dioxide from respiratory gases, comprising:

a base having a substantially planar upper surface and a side wall depending therefrom;

a cannister for containing a charge of carbon dioxide absorbing material and having upper inlet and lower outlet openings for permitting flow of gases therethrough in contact with said absorbing material;

a gasket formed of resiliently deformable material positioned on said upper surface for supporting said cannister, said gasket having an opening bounded by a raised annular lip for providing a fluid seal with said cannister outwardly of said outlet opening;

a cover removably attached in fluid sealed relationship to said base in a spaced surrounding relationship to said cannister thereby enclosing said cannister, said cover and said cannister cooperating to provide a fluid flow passage therebetween with said fluid flow passage being arranged for flow communication with said inlet opening;

inlet passage means in said base and passing through said side wall and said upper surface for flow communication with said fluid flow passage for supplying the same with gases from which carbon dioxide is to be removed;

opening means in said base arranged for flow communication with said outlet opening through said opening of said gasket;

outlet passage means in said base in fluid communication with said opening means for withdrawing gases from which carbon dioxide has been removed; and an auxiliary gas supply passage in said base and passing through said side wall for flow communication with said opening means.

9. The apparatus according to claim 8, further comprising latch means on said cover and said base for securing said cover to said base and for compressing said gasket.

10. A carbon dioxide absorbing apparatus of the type adapted to be placed in flow communication with a patient face mask or the like through a pair of breathing tubes, said apparatus comprising:

a base having an upper surface;

a pair of passage means extending within the base and having first and second ends, one of said second ends opening centrally through said upper surface and the other of said second ends opening through said upper surface in an offset relationship to said one of said second ends;

a cup-shaped cannister for retaining a charge of carbon dioxide absorbing material, said cannister having a side wall bounding an open upper end of said cannister and a bottom wall formed with a centrally located opening for permitting flow of gas through said cannister in contact with said material, said bottom wall having screen means for constraining passage of said material downwardly through said centrally located opening thereof;

a gasket formed of resiliently deformable material mounted on said upper surface, said gasket having a centrally located opening arranged for alignment with said one of said second ends and an offset opening arranged for alignment with said other of said second ends, said gasket including an annular raised portion surrounding said centrally located opening thereof, said cannister being removably supported in fluid sealing engagement on said gasket with said bottom wall spaced outwardly of said upper surface and said annular raised portion sealingly engaging said bottom wall about said centrally located opening of said cannister;

a cover;

means for removably attaching said cover to said base in fluid sealed engagement with said gasket and in a spaced surrounding relationship to said cannister thereby enclosing said cannister, said cover and said cannister cooperating to define a fluid flow passage therebetween, said offset opening being in flow communication with said passage and thereby with said open upper end of said cannister; and a pair of check valve means for placing said first ends of each of said pair of passage means in flow communication with each of said breathing tubes and for providing one way flow of gas through said apparatus between said breathing tubes.

11. An apparatus according to claim 10, wherein positioning means are provided for aligning said centrally located opening of said cannister with said centrally located opening of said gasket, and said positioning means includes pins arranged to upstand from said base within the last said passage for engagement with said side wall of said cannister.

12. An apparatus according to claim 4, wherein said pins are removably fixed to said base and extend upwardly through said gasket for removably securing said gasket to said base.

13. An apparatus according to claim 10, wherein said raised portion of said gasket comprises a raised annular lip arranged in surrounding relationship to said centrally located opening of said gasket for fluid sealing supporting engagement with said bottom wall of said cannister.

14. An apparatus according to claim 10, 12 or 13, wherein said cannister and said cover are formed at least in part of transparent material for affording view of said carbon dioxide absorbing material in said cannister, said base has a side wall depending from said upper surface, and a bottom surface, said upper surface and said bottom surface are substantially planar, said pair of check valve means are fixed to and said first ends of said pair of passages open through said side wall of said base, and there is additionally provided a flexible gas reservoir supported to depend from said base and an auxiliary gas supply passage extending within said base, and one of said pair of passage means includes a passage arranged in flow communication with said supply passage and to open through said bottom surface for flow communication with said flexible gas reservoir.

* * * * *

UNITED STATES PATENT AND TRADEMARK OFFICE
CERTIFICATE OF CORRECTION

PATENT NO. : 4,353,366

DATED : October 12, 1982

INVENTOR(S) : Allan M. Bickford

It is certified that error appears in the above–identified patent and that said Letters Patent are hereby corrected as shown below:

Col. 5, Line 60 - After "one-" - Please insert --- way ---.

Col. 8, Line 40 - Please change "4" to --- 11 ---.

Signed and Sealed this

Eleventh Day of January 1983

[SEAL]

Attest:

GERALD J MOSSINGHOFF

Attesting Officer     Commissioner of Patents and Trademarks